United States Patent [19]

Haslam et al.

[11] Patent Number: 4,880,631

[45] Date of Patent: Nov. 14, 1989

[54] CONTROLLED POROSITY OSMOTIC PUMP

[75] Inventors: John L. Haslam; Gerald S. Rork, both of Lawrence, Kans.

[73] Assignee: Merck & Co., Inc., Rahway, N.J.

[21] Appl. No.: 100,665

[22] Filed: Sep. 24, 1987

[51] Int. Cl.$^4$ ............................................. A61K 31/55
[52] U.S. Cl. ................................... 424/424; 424/426; 424/457; 424/468; 424/472
[58] Field of Search ............... 424/468, 471, 424, 426, 424/457–462, 469

[56] References Cited

U.S. PATENT DOCUMENTS

| | | |
|---|---|---|
| 3,538,214 | 11/1970 | Polli et al. |
| 3,845,770 | 11/1974 | Bardani |
| 3,916,899 | 11/1975 | Theeuwes et al. |
| 3,957,523 | 5/1976 | Ohno et al. |
| 4,160,452 | 7/1979 | Theeuwes |
| 4,200,098 | 4/1980 | Ayer et al. |
| 4,244,941 | 1/1981 | Lerk |
| 4,256,108 | 3/1981 | Theeuwes |
| 4,285,987 | 8/1981 | Ayer et al. |
| 4,326,525 | 4/1982 | Swanson et al. |
| 4,696,924 | 9/1987 | Marcoux ........................... 514/211 |
| 4,747,845 | 5/1988 | Korol ................................ 424/443 |

OTHER PUBLICATIONS

J. Pharm. Sci, 72, 772–775.

*Primary Examiner*—Nancy A. B. Swisher
*Attorney, Agent, or Firm*—Joseph F. DiPrima; Michael C. Sudol, Jr.

[57] ABSTRACT

The instant invention is directed to an osmotic pump, for the controlled release of diltiazem L-malate to an environment of use, said pump comprising:

(A) a core which comprises a therapeutically effective amount of diltiazem L-malate and an effective buffering amount of sodium bitartrate surrounded by (B) a rate controlling water insoluble wall, having a fluid permeability of $6.96 \times 10^{-18}$ to $6.96 \times 10^{-14}$ cm$^3$ sec/g and a reflection coefficient of less than 0.5, prepared from:
  (i) a polymer permeable to water but impermeable to solute and
  (ii) 0.1 to 60% by weight, based on the total weight of (i) and (ii), of at least one pH insensitive pore forming additive dispersed throughout said wall.

20 Claims, 7 Drawing Sheets

CONTROLLED POROSITY OSMOTIC PUMP

BACKGROUND OF THE INVENTION

Diltiazem hydrochloride is a calcium ion influx inhibitor which is commercially utilized in the treatment of angina pectoris due to coronary artery spasm and chronic stable angina.

Controlled delivery devices for therapeutically active agents are well known in the art. Generally, these devices may be characterized as either diffusion controlled delivery systems or osmotic dispensing devices. U.S. Pat. No. 3,538,214 discloses a diffusion controlled device in which a tablet core containing an active ingredient is surrounded by a water insoluble coating which contains film modifying agent soluble in the external fluids in the gastrointestinal tract. An example of an osmotic device is described in U.S. Pat. Nos. 3,845,770 and 3,916,899 which is a core composition of an active agent and an osmotically effective solute which is enclosed by an insoluble semipermeable wall having a release means. Numerous modifications to these types of delivery devices have been described in the art in an effort to improve their release characteristics.

The use of pore formers in substantially water impermeable polymers, such as polyvinyl chloride, is disclosed in J. Pharm. Sci. 72, 772-775 and U.S. Pat. No. 4,244,941. The devices release the core contents by simple diffusion through the pores in the coating.

U.S. Pat. No. 3,957,523 discloses a device which has pH sensitive pore formers in the wall.

U.S. Pat. No. 4,256,108; 4,160,452; 4,200,098 and 4,285,987 disclose devices with pore formers in only one of at least two wall layers. These devices contain a drilled hole for the release of the core contents.

Co-pending U.S. Pat. applications Attorney Docket Number IX112IB and IX112IC disclose systems which comprise an inner core compartment of osmotically active composition surrounded by an enclosing controlled porosity wall material that is substantially permeable to both solute and external fluid. These systems are osmotic dispensing devices for a broad range of therapeutically active agents. However, the delivery of a highly soluble agent from these devices at a constant rate is difficult to achieve.

U.S. Pat. No. 4,326,525 addresses the problem of delivering an active agent from an osmotic device by incorporating into the core a buffer which enters into a proton-transfer or neutralization reaction with the agent thereby producing an aqueous soluble agent salt within the device.

BRIEF DESCRIPTION OF THE INVENTION

This invention concerns an osmotically activated system for dispensing diltiazem L-malate, as the pharmacologically active agent, to biological receptor sites over a prolonged period of time. The system comprises an inner core compartment of osmotically active composition surrounded by an enclosing wall material. The core comprises diltiazem L-malate and sodium bitartrate, which exhibit unique solubility characteristics in an external fluid, and an osmotic pressure gradient across the wall against the external fluid. The wall constitutes a layer of controlled porosity that is substantially permeable to both the external fluid and the aqueous solution of the core composition. Diltiazem L-malate and sodium bitartrate are released from the system in a nearly pH independent manner by external fluid imbibition through the wall into the inner core compartment at a rate controlled by the wall composition and dimensions, producing a solution containing core composition that is released through the wall at a controlled rate in response to fluid volume flux, dV/dt, resulting from the osmotic pressure gradient, and diffusive flux, $(dM/dt)_D$, driven by the chemical potential gradient of the core composition across the wall. The total rate of release, $(dM/dt)_T$ is given by Equation 1 where C is the concentration $$\left(\frac{dM}{dt}\right)_T = \frac{dV}{dt}(C) + \left(\frac{dM}{dt}\right)_D \qquad \text{Eq. 1}$$

of the active agent in the dissolved core composition and remains constant when excess solid core mass is present. In the present invention the volume flux contribution, $(dV/dt)C$, to the total rate is expected to be greater than the diffusive contribution, $(dM/dt)_D$, and forms the basis for the osmotic pump action of the device.

The present invention include osmotic systems that are readily manufactureable to deliver a pre-determined dose of agent at a programmed rate from compositions of matter in the varied geometries and sizes of tablets, and such related dosage forms as familiar to those skilled in the art for oral, buccal, vaginal, rectal, nasal, ocular, parenteral and related routes of administration. The invention also provides osmotic systems that deliver agent on an equivalent mass per unit surface area basis.

A BRIEF DESCRIPTION OF THE DRAWINGS

DETAILED DESCRIPTION OF THE INVENTION

The instant invention is directed to an osmotic pump, for the controlled release of diltiazem L-malate to an environment of use, said pump comprising:

(A) a core which comprises a therapeutically effective amount of diltiazem L-malate and an effective buffering amount of sodium bitartrate surrounded by (B) a rate controlling water insoluble wall, having a fluid permeability of $6.96 \times 10^{-18}$ to $6.96 \times 10^{-14}$ cm$^3$ sec/g and a reflection coefficient of less than 0.5, prepared from:
  (i) a polymer permeable to water but impermeable to solute and
  (ii) 0.1 to 60% by weight, based on the total weight of (i) and (ii), of at least one pH insensitive pore forming additive dispersed throughout said wall.

Figure 1:
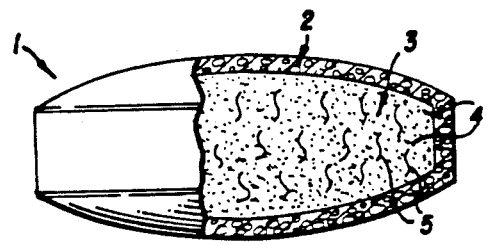
FIG. 1 is an embodiment of the osmotic pump.

The osmotically active core composition mass (3) of FIG. 1, is typically in the form of a solid conventional tablet. The core is completely encased by the controlled porosity wall (2). The core is comprised of a mixture of diltiazem L-malate and sodium bitartrate, as well as other inert pharmaceutically acceptable carriers, which are not osmotically effective agents (4, 5, etc.) combined to give the desired manufacturing and ultimate agent(s) delivery characteristics.

The preferred specifications for the core are summarized below and include:

| | | |
|---|---|---|
| 1. | Core Loading (size) | 0.05 nanograms to 5 grams or more (includes dosage forms for humans and animals) |
| 2. | Osmotic pressure developed by a solution of the core | about 10-22 atmospheres are developed from the mixture of diltiazem L-malate and sodium bitartrate; however osmotic pressures greater than zero are within guidelines |
| 3. | Core solubility | to get continuous, uniform release (zero-order kinetics) of 50% or greater of the initially loaded core mass, the ratio of the core mass solubility, S, to the core mass density, $\rho$, that is S/$\rho$, must be 0.5 or lower. Typically this occurs when 50% of the initially loaded core mass saturates a volume of external fluid equal to the total volume of the initial core mass. |

S/$\rho$ ratios less than 0.5 fall within the workings of the invention and result in higher percentages of initial core mass delivered under zero-order kinetics. S/$\rho$ can be selected to give acceptable combined characteristics of stability, release rate, and manufacturability.

In the present invention diltiazem L-malate, as the active agent, when combined with an effective buffering amount of sodium bitartrate has the desired solubility, osmotic pressure, density, stability, and manufacturability characteristics. The effective buffering amount of sodium bitartrate is an amount sufficient to: (a) provide greater than 50% of the drug release zero order and (b) hold the pH dependence of drug release to less than ±20% when the percent drug release in water is compared with drug release over the pH range of 1.2 to 7.5. About 80 percent by weight of sodium bitartrate to diltiazem L-malate has been found to be the minimum amount sufficient as an effective buffering amount.

There is no critical upper limit as to the total amount of drug plus buffer that can be incorporated into a core mass and typically will follow the core loading (size) specification 1. However, the maximum amount of diltiazem L-malate contained in the core composition should not exceed the amount which is necessary to deliver the equivalent amount of diltiazem hydrochloride recommended for approved therapeutic uses. The lower limit ratio of diltiazem L-malate and sodium bitartrate to other inert pharmaceutically acceptable carriers is dictated by the desired osmotic activity of the core composition, the desired time span of release, and the pharmacological activity of the active agent. Generally the core will contain 0.01% to 90% by weight or higher, of a mixture of diltiazem L-malate, as the active agent and sodium bitartrate with other inert pharmaceutically acceptable carriers. The solubilized constituents create a water activity gradient across the wall, (2), of FIG. 1, resulting in osmotically actuated fluid movement constituting the osmotic pump action of the invention.

The amount of diltiazem L-malate, as the active agent and sodium bitartrate alone or admixed with other inert pharmaceutically acceptable carriers present in the device is initially in excess of the amount that can be dissolved in the fluid that enters the reservoir. Under this physical state when the agent is in excess, the device will osmotically operate to give a substantially constant rate of release. The rate of agent release pattern can also be varied by having different amounts of agent in the reservoir to form solutions containing different concentrations of agent for delivery from the device. Generally, the device can house from 0.05 ng to 5 grams or more, with individual devices containing, for example, 25 ng, 1 mg, 5 mg, 250 mg, 500 mg, and the like.

As a specific embodiment of the present invention, the diltiazem L-malate in the core is between 30 and 500 mg and as another specific embodiment of the present invention, the sodium bitartrate in the core is between 30 and 500 mg.

The resulting device will have a water permeability driven by a saturated solution of diltiazem L-malate, as the active agent and sodium bitartrate at the temperature of use, of 0.01 ml per $cm^2$ of surface area per day to 10 ml per $cm^2$ of surface area per hour.

The controlled porosity wall of the present invention is substantially permeable to both solute and external fluid. The wall is composed of materials that maintain their physical and chemical integrity during the controlled dispensing of agent in mixture with materials that can be leached into the external fluid. The wall has programmable fluid transmission rate which provide for controlled release of agent which is nearly free from environmental influences including pH and degree of external fluid agitation.

The wall may be composed of either insoluble, nonerodible materials mixed with leachable additives, or bioerodible materials containing leachable additives. Bioerodible materials would be selected to bioerode after a predetermined period with bioerosion occurring subsequent to the period of agent release.

The phrase "permeable to water but impermeable to solutes" means the water permeates through the polymer preferably to solute, under a pressure differential.

Referring to FIG. 1, the osmotic pump device (1) is typically in the form of a single coated tablet or shaped for rectal or vaginal applications.

The water insoluble, permeable wall (2) of controlled porosity may be applied to osmotically active core composition masses (3) by spray coating procedures. The wall is comprised of (a) polymeric material that is insoluble in the fluids of the environment of intended use (usually water); (b) other added excipients that will dissolve in the environmental fluids and leach out of the wall. The leached wall is a sponge-like structure composed of numerous open and closed cells that form a discontinuous interwoven network of void spaces when viewed with a scanning electron microscope. This controlled porosity wall serves as both the water entry and core composition solution exit sites. The wall is permeable to both water and solutes, and as constituted in the environment of use has a small solute reflection coefficient, $\sigma$, and displays poor semipermeable characteristics when placed in a standard osmosis cell.

The specifications for the wall are summarized below and include:

| 1. | Fluid Permeability of the wall | $6.96 \times 10^{-18}$ to $6.96 \times 10^{-14}$ cm$^3$ sec/g (equivalent to $10^{-5}$ to $10^{-1}$ cm$^3$ mil/cm$^2$ hr atm) |
| --- | --- | --- |
| 2. | Reflection Coefficient | Microporous coats to have a reflection coefficient, $\sigma$, defined as: |

$$\sigma = \frac{\text{x osmotic volume flux}}{\text{osmotic pressure difference}} \times \frac{\text{hydrostatic pressure difference}}{\text{hydrostatic volume flux}}$$ where $\sigma$ is less than 1, usually 0 to 0.8.

A specific embodiment of the present invention are those osmotic pumps wherein the reflection coefficient of the wall is less than 0.5. Exemplifying this embodiment are those osmotic pumps wherein the reflection coefficient of the wall is less than 0.1.

Additional, preferred specifications for the wall include:

| 1. | Plasticizer and Flux Regulating Additives | 0 to 50, preferably 0.001 to 50, parts per 100 parts wall material |
| --- | --- | --- |
| 2. | Surfactant Additives | 0 to 40, preferably .001 to 40, parts per 100 parts wall material |
| 3. | Wall Thickness | 1 to 1,000, preferably 20 to 500, microns typically although thinner and thicker fall within the invention |
| 4. | Microporous Nature | 5% to 95% pores between 10 angstroms and 100 microns diameter |
| 5. | Pore forming Additives | 0.1 to 60%, preferably 0.1 to 50%, by weight, based on the total weight of pore forming additive and polymer, pH insensitive pore forming additive, preferably: (a) 0.1 to 50%, preferably 0.1 to 40%, by weight solid additive (b) 0.1 to 40% by weight liquid additive But no more than 60% total pore formers. |

The water insoluble wall of the instant invention must not be covered on its inner or outer surface by a layer of material that is impermeable to dissolved solutes within the core during the period of pumping operation.

Any polymer film by itself permeable to water but impermeable to solutes as previously defined may be used. However, the film may be covered initially by a rapidly dissolving coat used for aesthetic purposes or containing a second drug substance. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4% cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethyl cellulose hydroxylated ethylenevinylacetate, poly (ortho ester)s, polyacetals, semipermeable polyglycolic or polylactic acid and derivatives thereof, selectively permeable associated polyelectrolytes, polymers of acrylic and methacrylic acid and esters thereof. film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

A controlled porosity wall can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used.

Any pH insensitive pore forming additives may be used in the instant invention. The microporous wall may be formed in situ, by a pore-former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers than can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like. The alkaline earth metal salts such as calcium chloride, calcium nitrate, and the like. The transition metal salts such as ferric chloride, ferrous sulfate, zinc sulfate, cupric chloride, and the like. Water may be used as the pore-former. The pore-formers include organic compounds such as saccharides. The saccharides include the sugars sucrose, glucose, fructose, mannose, galactose, aldohexose, altrose, talose, lactose, monosaccharides, disaccharides, and water soluble polysaccharides. Also, sorbitol, mannitol, organic aliphatic and aromatic oils, including diols and polyols, as exemplified by polyhydric alcohols, poly(alkylene glycols), polyglycols, alkylene glycols, poly($\alpha,\omega$)alkylenediols esters or alkylene glycols poly vinylalcohol, poly vinyl pyrrolidone, and water soluble polymeric materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of inorganic and organic salts, carbohydrates, polyalkylene glycols, poly($\alpha, \omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

It is generally desirable from a preparation standpoint to mix the polymer in a solvent. Exemplary solvents suitable for manufacturing the wall of the osmotic device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof.

Exemplary plasticizers suitable for the present purpose include plasticizers that lower the temperature of the second-order phase transition of the wall or the elastic modulus thereof; and also increase the workability of the wall, its flexibility and its permeability to fluid. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, sulfonamides, and halogenated phenyls. Generally, from 0.001 to 50 parts of a plasticizer or a mixture of plasticizers are incorporated into 100 parts of wall forming material.

Suitable plasticizers can be selected for blending with the wall forming materials by selecting plasticizers that have a high degree of solvent power for the materials, are compatible with the materials over both the processing and use temperature range exhibit permanence as seen by their strong tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter $\chi$, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability of flux through the wall. The agent can be preselected to increase or decrease the liquid flux. Agents that produce a marked increase in permeability to fluid such as water, are often essentially hydrophilic, while those that produce a marked decrease to fluids such as water, are essentially hydrophobic. The flux regulators in some embodiments also can increase the flexibility and porosity of the lamina. Examples of flux regulators include polyhydric alcohols and derivatives thereof, such as polyalkylene glycols of the formula H—(O—alkylene)$_n$—OH wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula H—(OCH$_2$CH$_2$)$_n$—OH wherein n is respectively 5 to 5.7, 8 2 to 9.1, 12.5 to 13.9, 29 to 36, 29.8 to 37, 68 to 84, and 158 to 204. Other polyglycols include the low molecular weight glycols such as polypropylene, polybutylene and polyamylene.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present purpose are those surfactants, when added to a wall forming material and other materials, aid in producing an integral composite that is useful for making the operative wall of a device. The surfactants act by regulating the surface energy of materials to improve their blending into the composite. This latter material is used for manufacturing devices that maintain their integrity in the environment of use during the agent release period. Generally, the surfactants are amphoteric molecules comprised of a hydrophobic part and a hydrophilic part. The surfactants can be anionic, cationic, nonionic or amphoteric, and they include anionics such as sulfated esters, amides. alcohols, ethers and carboxylic acids; sulfonated aromatic hydrocarbons, aliphatic hydrocarbons, esters and ethers; acylated amino acids and peptides; and metal alkyl phosphates; cationic surfactants such as primary, secondary, tertiary and quaternary alkylammonium salts; acylated polyamines; and salts of heterocyclic amines, arylammonium surfactants such as esters of polyhydric alcohols; alkoxylated amines; polyoxyalkylene; esters and ethers of polyoxyalkylene glycols; alkanolamine fatty acid condensates; tertiary acetylamic glycols; and dialkyl polyoxyalkylene phosphates; and ampholytics such as betamines; and amino acids.

The osmotic pump according to the present invention may also further comprise an external layer of a pharmaceutically acceptable carrier and a therapeutically effective amount of a cardiovascular agent.

Illustrative of such an osmotic pump according to the present invention are those in which the cardiovascular agent is selected from alpha receptor blocking agents, alpha and beta receptor blocking agents, angiotensin converting enzyme inhibitors, antianginal agents, antiarrhythmics, antiembolus agents, antihypertensives, beta blocking agents, digitalis, hemorheologic agents, inotropic agents, myocardial infarction prophylaxis, quinidine, cerebral vasodilators, coronary vasodilators, peripheral vasodilators, and vasopressors.

Exemplifying such an osmotic pump according to the present invention are those in which the cardiovascular agent is selected from angiotensin converting enzyme inhibitors. Such angiotensin converting enzyme inhibitors include, without limitation, captopril, enalapril and lisinopril.

The following examples illustrate the preparation of the drug-delivery devices of this invention and their controlled release of one or more therapeutically active ingredients into an environment of use and as such are not to be considered as limiting the invention set forth in the claims appended hereto.

EXAMPLE 1

Tablet for the osmotically controlled release of the beneficial drug diltiazem were made as follows: to a mixing bowl was added 262 g of diltiazem L-malate and 305 sodium bitartrate monohydrate which were then mixed. A solution of 37 g of Povidone K29–32 was prepared in 92 g of water and then added to the powders while mixing. The resultant dough was passed through an extruder using an 0.5 mm screen onto a tray and let dry overnight.

The granulation was then dried for 6 hours at 60° C. The dry granulation was forced through a series of screens to a final 30 mesh screen. Some of this material (67.3 g) was then mixed with 1.4 g of purified stearic acid USP for one minute. Tablets were prepared using a Stokes ® Model F press fitted with ⅜ inch deep concave punches. The tablet weight was 340 mg.

Fifty of these tablets were coated in a small pan coater (8" HCT-Mini Hi-Coater ®) along with 400 cc of filler tablets (5/16" tablets made with lactose, starch, Avicel ® PH101and magnesium stearate). The coating solution was prepared by adding 18 g of cellulose acetate (CA-320S) and 18 g of cellulose acetate (CA-394–60S) to a 4 l erlenmeyer flask containing 490 ml of methylene chloride. After all the polymer particles were dispersed, 300 ml of methanol was added and the solution stirred and warmed to dissolve the polymers.

The 19 g of Sorbitol was dissolved in a 250 ml erlenmeyer flask by the addition of 40 ml of water and 130 ml of methanol. This solution was added to the polymer solution slowly with mixing. Finally 7.2 g of polyethylene glycol 400 was added and thoroughly mixed to give the final coating solution.

The filler and active tablets were placed in the coating pan and heated air was passed through the tablet bed. The pan was rotated at 28 rpm. When the outlet temperature reached 30° C., the coating solution was applied through a atomizing nozzle at 20 ml/min with atomizing air at 1.4 Kg/cm$^2$. The inlet air temperature was maintained between 60°–70° C. to keep the outlet temperature at 30° C. Sufficient coating solution (800–900 ml) was applied to give approximately 300 micron coat on the active tablets. The active tablets were then dried in an oven for 18 hours at 45° C.

Figure 2:
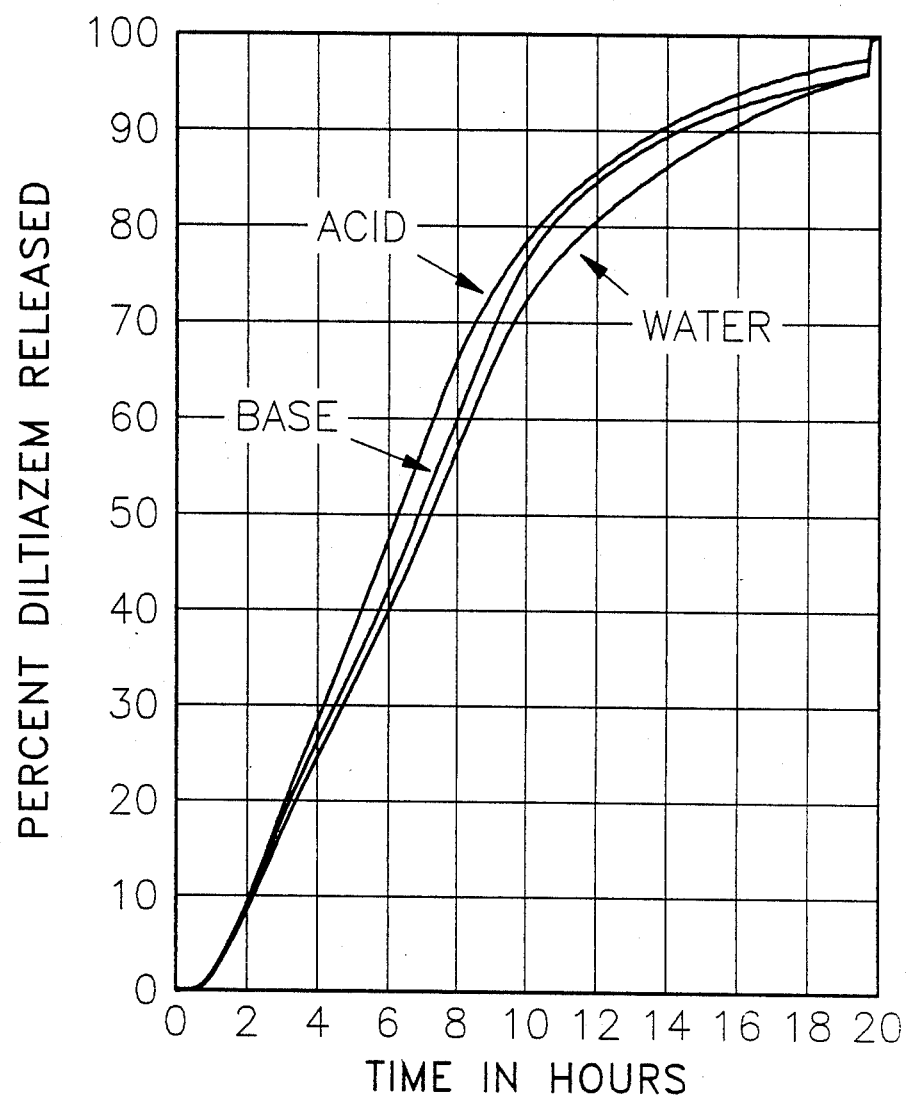
FIG. 2 is the release profile (statistical average of several pumps) of the pumps produced in Example 1.

The release profiles of these tablets in pH 1.2 hydrochloric acid (with 2 g/l of sodium chloride), water, and a 0.05M phosphate solution at pH 7.5 are shown in FIG. 2. A standard USP dissolution setup was used with a stirring rate of 100 rpm and bath temperature of 37° C. Continuous flow UV monitoring at 270 nm of diltiazem was used. The percent release was calculated from the final reading after the tablets were broken open.

EXAMPLE 2

To show the beneficial effect of the sodium bitartrate another batch of tablets was prepared without the sodium bitartrate. A wet granulation of 9 g of diltiazem L-malate was prepared by adding an aqueous solution of 0.8 g povidone K29-32 in 3.5 ml of water. This was forced through a number 14 mesh screen and let dry several hours at 30° C. and then overnight at 60° C. The material was then forced through several screens, the final one being 25 mesh. The purified stearic acid USP (160 mg) was added to 8 g of the dry granulation and mixed in a bottle. Tablets were made using a Stokes ® Model F press with ¼ inch deep concave punches. The tablet weight was 156 mg.

These tablets were coated using the same coating procedure described in Example 1 with the same coating solution formula. A coat of 81 microns was applied to these tablets which were then dried at 45° C. overnight.

Figure 3:
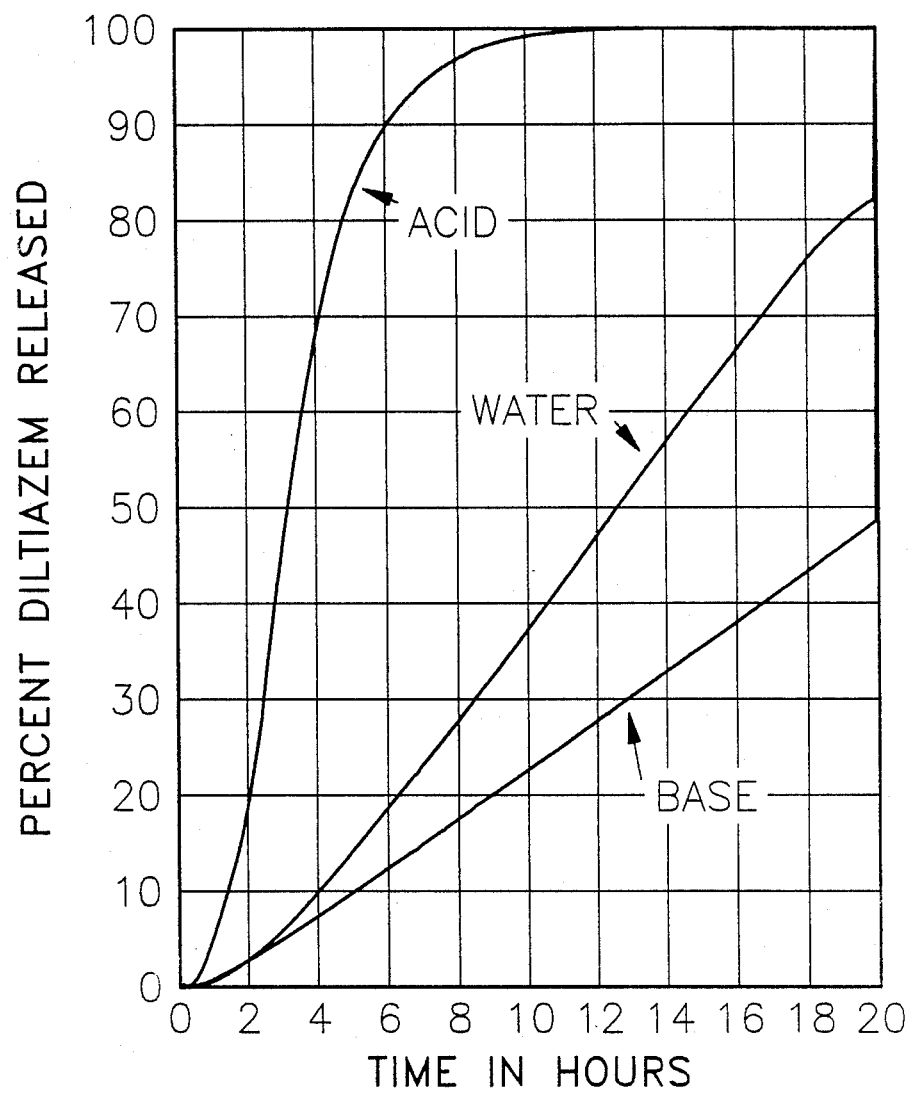
FIG. 3 is the release profile (statistical average of several pumps) of the pumps produced in Example 2.
Figure 4A:
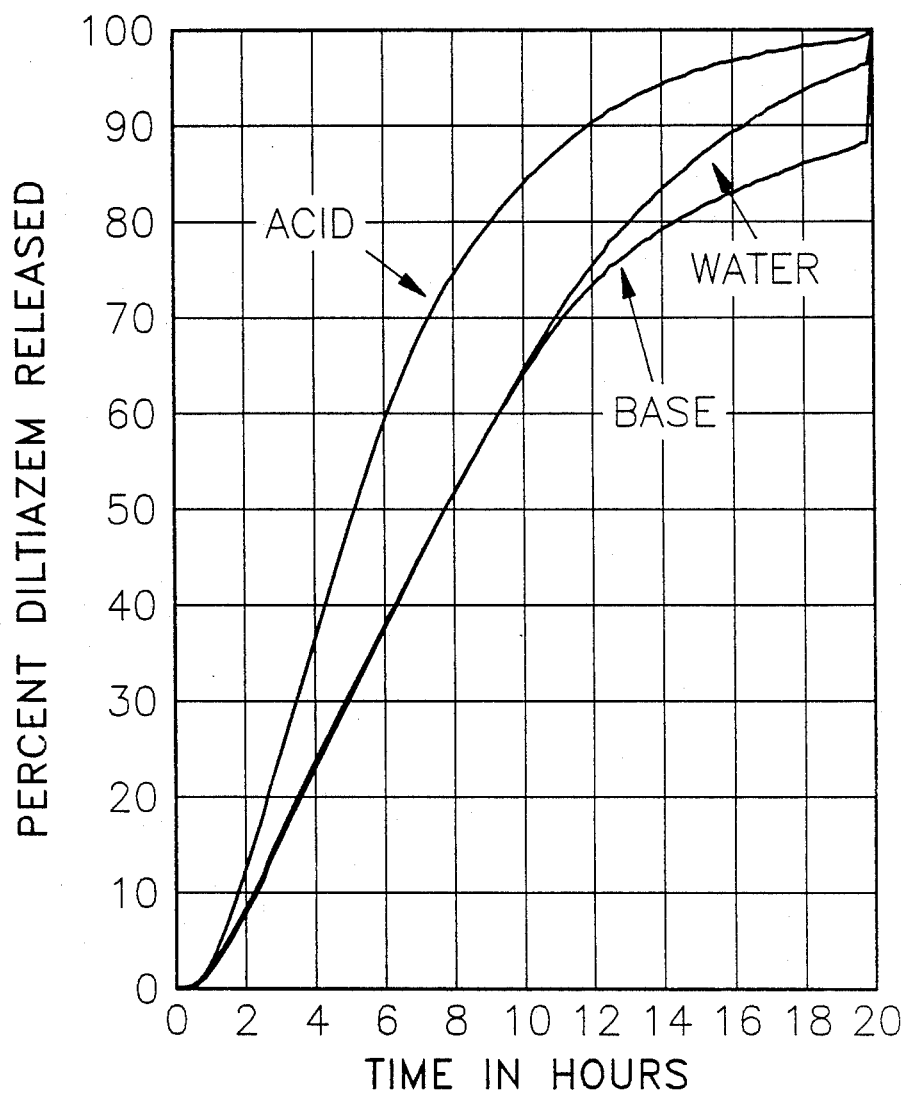
FIGS. 4A through 4D are the release profiles (statistical average of several pumps) of the pumps produced in Example 3 formulations 3A through 3D, respectively.
Figure 4B:
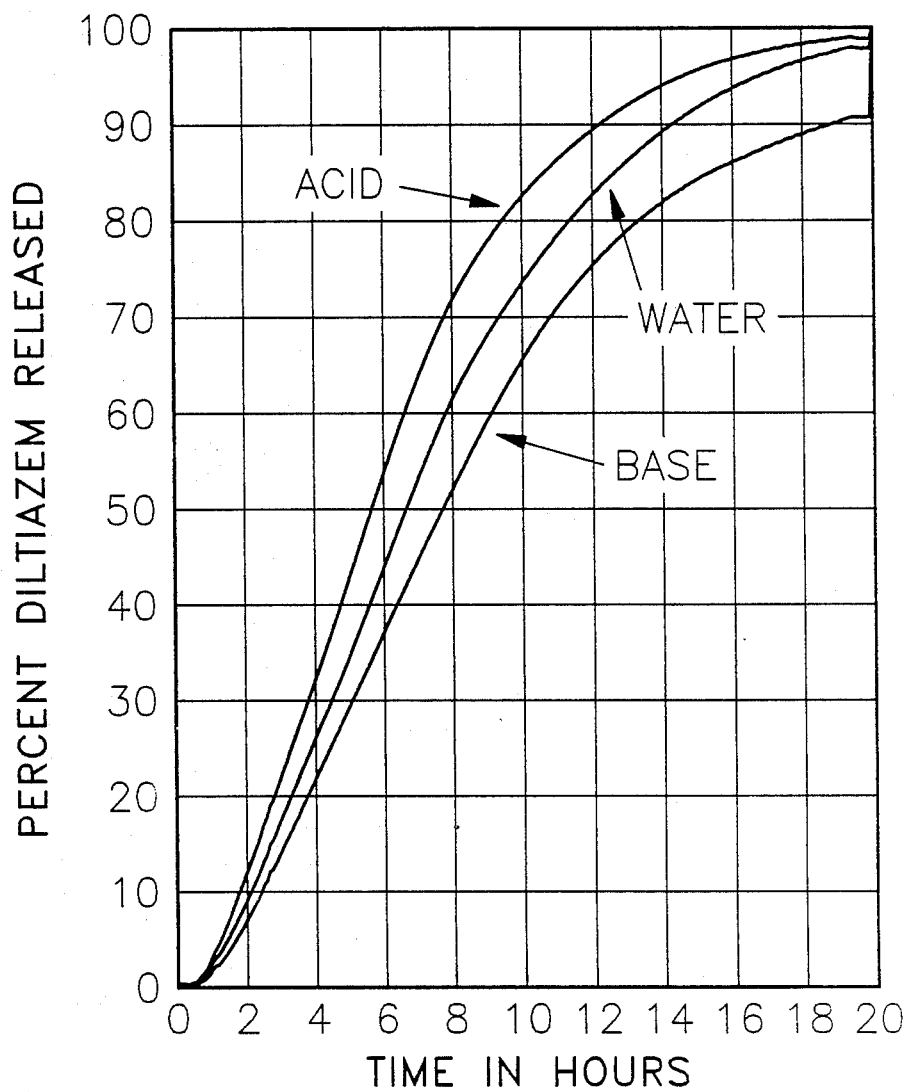
Figure 4C:
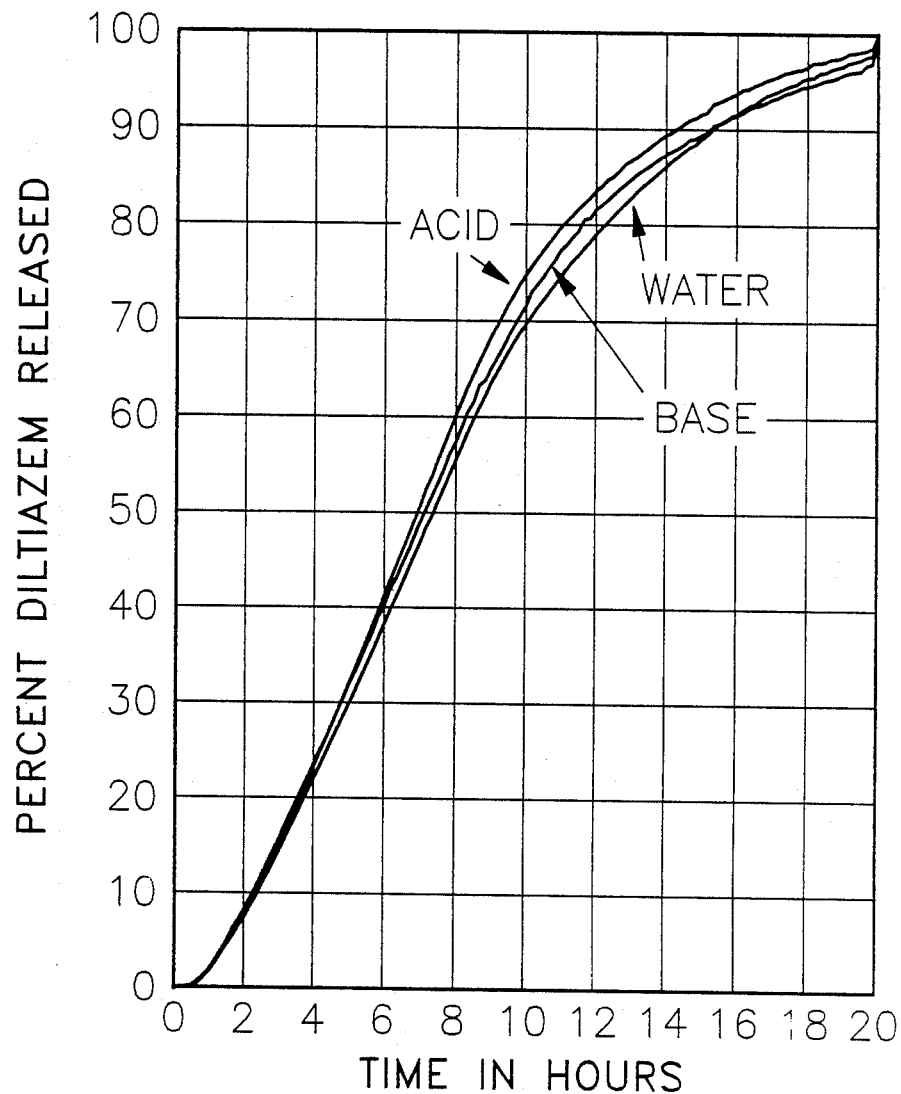
Figure 4D:
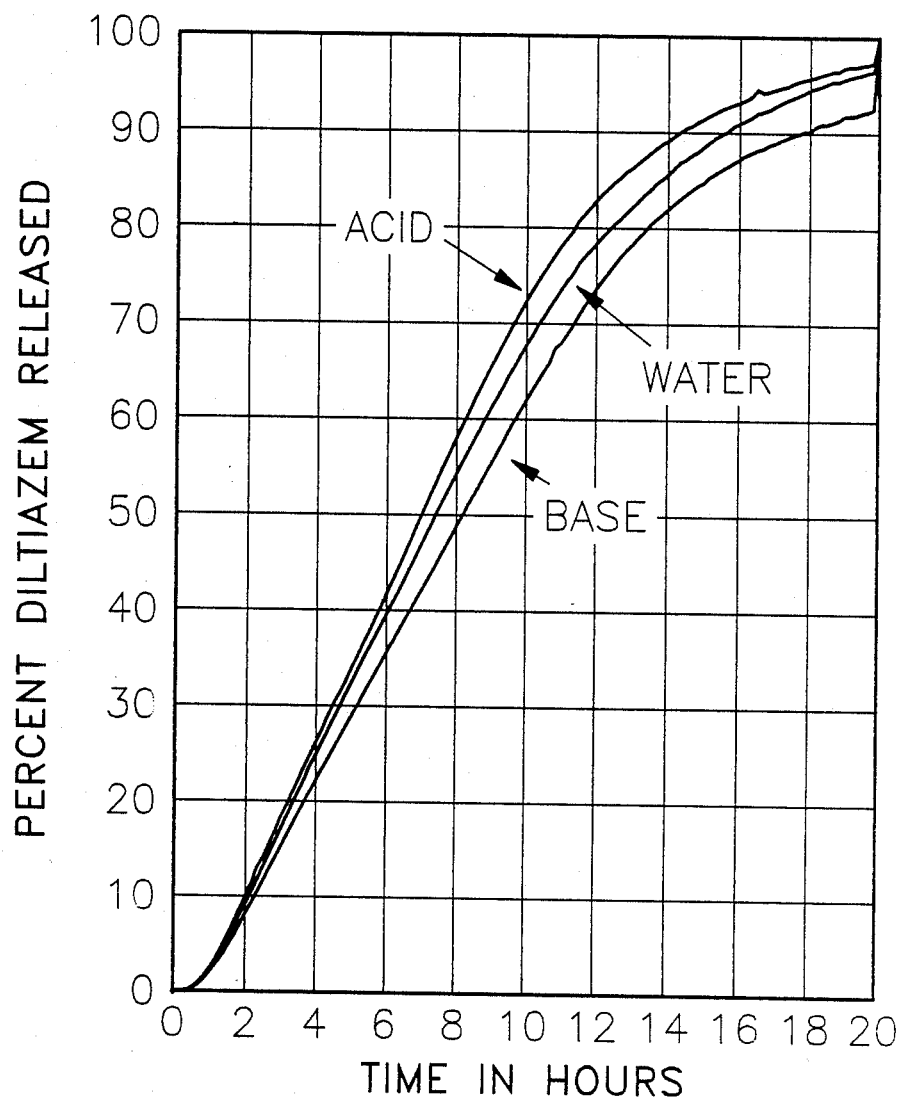

The release profile of the drug from these tablets are shown in Figure 3. The same release media and the same set-up as described in Example 1 were used. The effect of the sodium bitartrate in the tablet formulation can clearly be observed by the relative lack of pH dependence observed by comparing the release of drug between FIG. 2 (with sodium bitartrate) and FIG. 3 (without sodium bitartrate).

EXAMPLE 3

To better define the effective range of sodium bitartrate, a series of tablets with different ratios of diltiazem L-malate to sodium bitartrate were prepared. To a mixture of diltiazem L-malate and sodium bitartrate (see table below) was added 5.2 g of a solution of Povidone ® K29–32 (12 g) in water (40 g) and the resultant combination mixed until homogeneous.

| Formulation | Diltiazem L-malate (g) | Sodium Bitartrate (g) |
|---|---|---|
| 3A | 10 | 5 |
| 3B | 10 | 8 |
| 3C | 10 | 10 |
| 3D | 10 | 15 |

Each of the wet granulations was dried at 60° C. (or 4 hours and then forced through a series of screens, the final one being 30 mesh. Each of the dried granulations was weighed and 2 percent of stearic acid was added with mixing. This material was tableted using ⅜ inch deep concave punches to give tablets which contained approximately 146 mg of diltiazem L-malate.

The tablet weights were as follows:

| Formulation | |
|---|---|
| 3A | 233 mg |
| 3B | 292 mg |
| 3C | 315 mg |
| 3D | 380 mg |

The tablets were coated using the coating procedure described in Example 1. The coating thickness ranged from 365 to 435 microns.

The release profiles are shown in FIGS. 4A through 4D for the formulations 3A through 3D, respectively. The same release media and the same set-up as described in Example 1 was used.

From these results the percentage of sodium bitartrate by weight to diltiazem L-malate of about 80 percent is required to reduce the pH effects on the release profiles and thus represents the minimum effective buffering amount of sodium bitartrate. Amounts of sodium bitartrate of up to about 150 percent by weight have also been shown to be effective in buffering the pH effects on the release profiles.

EXAMPLE 4

To show how a cardiovascular agent such as enalapril can be combined with this diltiazem L-malate sodium bitratrate tablet the following example is given.

In view of the fact that enalapril is normally given on a once-a-day dose regimen a fast release of enalpril from the tablet would substitute for the present tablet. The fast release of enalpril would then be followed by the controlled release of diltiazem L-malate.

Diltiazem L-malate tablets were prepared as described in Example 1 and the release profiles determined as shown in FIG. 2. These tablets were then overcoated with the following solution.

| | |
|---|---|
| Water | 250 ml. |
| Hydroxypropyl methylcellulose E-5 | 12.5 g |
| Enalapril Maleate | 12.5 g |
| Sodium bicarbonate | 6.25 g |

A 400 ml beaker containing 150 ml of water was heated on a hot plate to 80° C. The HPMC-E5 was suspended in the hot water by vigorous stirring and then cooled in an ice water bath to room temperature. Stirring continued until complete solution was achieved. The enalapril maleate was suspended in 100 ml of water in a 400 ml beaker and small amounts of the sodium bicarbonate were added with stirring. Additional amounts were added as the effervescence slowed until all the bicarbonate was added. The enalapril solution was then added to the polymer solution and thoroughly mixed. This solution was applied to the diltiazem L-malate tablets using the pan coater described in Example 1. The conditions for coating this aqueous solution are as follows: 400 cc of filter tablets, inlet temperature 70°–80° C., outlet 32°–34° C., coating solution pumping rate, 4–5 ml/min, atomizing air pressure 1.6 kg/cm² and pan rotation 30 rpm.

The weight of the tablets was checked from time to time so that when 21–25 mg. was applied to the tablet (~ 10 mg enalapril maleate) the coating was terminated. The tablets were then dried 18 hours at 45° C. and then 4 hours at 60° C. to remove any remaining solvent.

The release properties were determined using the standard U.S.P. set up with paddle rotation at 100 rpm. The release of enalapril was very rapid with essentially all of the drug released in 5 minutes. The release profile of diltiazem from these tablets was not changed from that observed with tablets not coated with HPMC E-5 and enalapril maleate.

What is claimed is:

1. An osmotic pump, for the controlled release of diltiazem L-malate to an environment of use, said pump comprising:
   (A) a core which comprises a therapeutically effective amount of diltiazem L-malate and between 80 and 150 percent by weight of sodium bitartrate surrounded by
   (B) a rate controlling water insoluble wall, having a fluid permeability of $6.96 \times 10^{-18}$ to $6.96 \times 10^{-14}$ cm³ sec/g and a reflection coefficient of less than 0.5, prepared from:
      (i) a polymer permeable to water but impermeable to solute and
      (ii) 0.1 to 60% by weight, based on the total weight of (i) and (ii), of at least one pH insensitive pore forming additive dispersed throughout said wall.

2. An osmotic pump according to claim 1 wherein the diltiazem L-malate in the core is between 30 and 500 mg.

3. An osmotic pump according to claim 1 wherein the sodium bitartrate in the core is between 30 and 500 mg.

4. An osmotic pump according to claim 1, wherein said pore forming additive comprises:
   (a) 0.1 to 50%, by weight, solid additive, based on the total weight of (i) and (ii), and/or
   (b) 0.1 to 40%, by weight, liquid additive, based on the total weight of (i) and (ii), not to exceed a total weight % of pore forming additive of 60%.

5. An osmotic pump according to claim 4 wherein said wall is 20 to 500 microns thick and said wall pores are between 10 angstroms and 25 microns in diameter.

6. An osmotic pump according to claim 1, wherein said reflection coefficient is less than 0.1.

7. An osmotic pump according to claim 1, further comprising:
   (C) 0 to 50 parts per 100 parts of (i) and (ii) of plasticizer and flux regulating additives and
   (D) 0 to 40 parts per 100 parts of (i) and (ii), of surfactant additive.

8. An osmotic pump according to claim 1, wherein said water insoluble wall is 1 to 1,000 microns thick and wherein 5 to 95% of the resulting wall pores are between 10 angstroms and 100 microns in diameter.

9. An osmotic pump according to claim 1, wherein said polymer is selected from the group consisting of cellulose esters, acylated polysaccharides, polyurethane, polymers of acrylic and methacrylic acid and esters thereof, poly (ortho ester)s, polyacetals and mixtures thereof.

10. An osmotic pump according to claim 9, wherein said polymer is selected from the group consisting of cellulose esters and acylated polysaccharides.

11. An osmotic pump according to claim 9, wherein said polymer is selected from the group consisting of polyurethanes and polymers of acrylic and methacrylic acid and esters thereof.

12. An osmotic pump according to claim 9, wherein said polymer is selected from the group consisting of poly(ortho ester)s and polyacetals.

13. An osmotic pump according to claim 1, wherein said pore forming additive is selected from the group consisting of water, alkali metal salts, alkaline earth metal salts, saccharides, aliphatic polyols, aromatic polyols and mixtures thereof.

14. An osmotic pump according to claim 1, wherein 0.1 to 50%, by weight, of said pore forming additive is used.

15. An osmotic pump according to claim 1, wherein said pH insensitive pore forming additive is selected from the group consisting of polyethylene glycol, sorbitol, glucose and mixtures thereof.

16. An osmotic pump according to claim 1, further comprising:
    an external layer of a pharmaceutically acceptable carrier and a therapeutically effective amount of a cardiovascular agent.

17. An osmotic pump according to claim 16 wherein the cardiovascular agent is selected from alpha receptor blocking agents, alpha and beta receptor blocking agents, angiotensin converting enzyme inhibitors, antianginal agents, antiarrhythmics, antiembolus agents, antihypertensives, beta blocking agents, digitalis, hemorheologic agents, inotropic agents, myocardial infarction prophylaxis, quinidine, cerebral vasodilators, coronary vasodilators, peripheral vasodilators, and vasopressors.

18. An osmotic pump according to claim 17 wherein the cardiovascular agent is selected from angiotensin converting enzyme inhibitors.

19. An osmotic pump according to claim 18 wherein the angiotensin converting enzyme inhibitor is selected from captopril, enalapril and lisinopril.

20. An admixture of dilitiazem L-malate with between 80 and 150 percent by weight of sodium bitartrate in a drug delivery device for the controlled release of diltiazem L-malate to an environment of use.

* * * * *